US009167968B2

(12) United States Patent
Saeed et al.

(10) Patent No.: US 9,167,968 B2
(45) Date of Patent: Oct. 27, 2015

(54) APPARATUS TO MEASURE THE INSTANTANEOUS PATIENTS' ACUITY VALUE

(75) Inventors: Mohammed Saeed, Cambridge, MA (US); Larry Nielsen, Burlington, MA (US); Joseph J. Frassica, Westborough, MA (US); Walid S. I. Ali, Chandler, AZ (US); Larry J. Eshelman, Ossining, NY (US); Wei Zong, Croton-on-Hudson, NY (US); Omar Abdala, Waltham, MA (US)

(73) Assignee: Koninklijke Philips N.V., Eindhoven (NL)

(*) Notice: Subject to any disclaimer, the term of this patent is extended or adjusted under 35 U.S.C. 154(b) by 908 days.

(21) Appl. No.: 11/917,767

(22) PCT Filed: Jun. 13, 2006

(86) PCT No.: PCT/IB2006/051888
§ 371 (c)(1),
(2), (4) Date: Dec. 17, 2007

(87) PCT Pub. No.: WO2006/136972
PCT Pub. Date: Dec. 28, 2006

(65) Prior Publication Data
US 2008/0214904 A1 Sep. 4, 2008

Related U.S. Application Data

(60) Provisional application No. 60/692,754, filed on Jun. 22, 2005.

(51) Int. Cl.
*A61B 5/00* (2006.01)
*G06Q 50/22* (2012.01)
*G06F 19/00* (2011.01)

(52) U.S. Cl.
CPC .......... *A61B 5/0006* (2013.01); *G06F 19/3431* (2013.01); *G06F 19/3487* (2013.01); *G06Q 50/22* (2013.01); *G06F 19/322* (2013.01); *G06F 19/3406* (2013.01)

(58) Field of Classification Search
None
See application file for complete search history.

(56) References Cited

U.S. PATENT DOCUMENTS 5,331,549 A * 7/1994 Crawford, Jr. ................. 600/513
5,435,324 A * 7/1995 Brill .............................. 128/897
(Continued)

FOREIGN PATENT DOCUMENTS

EP  0707824 A2  4/1996
EP  0808603 A2  11/1997
WO  20050069969 A1  1/2005

OTHER PUBLICATIONS

GE Healthcare: Subacute General Care/Patient Monitoring Telemetry http://www.gemedicalsystemseurope.com/euen/monitor/homepage_subacute.html.
(Continued)

*Primary Examiner* — William Thomson
*Assistant Examiner* — Bobby Soriano

(57) ABSTRACT

In a patient monitoring system (10), shorter interval physiological parameters and longer interval clinical data are collected from a monitored patient (12). A composite acuity score generator (70) generates or updates a composite acuity score indicative of wellbeing of the patient (12) based at least on the sensed physiological parameters and the longer interval data. A monitor (22, 56) displays current values of at least one of selected sensed physiological parameters, longer interval data, and the composite acuity score.

32 Claims, 9 Drawing Sheets

(56) References Cited

U.S. PATENT DOCUMENTS

| | | | |
|---|---|---|---|
| 5,792,047 A | 8/1998 | Coggins | |
| 6,067,467 A | 5/2000 | John | |
| 6,193,654 B1* | 2/2001 | Richardson et al. | 600/300 |
| 6,317,700 B1* | 11/2001 | Bagne | 702/181 |
| 6,338,713 B1* | 1/2002 | Chamoun et al. | 600/300 |
| 6,440,066 B1* | 8/2002 | Bardy | 600/300 |
| 7,192,387 B2* | 3/2007 | Mendel | 482/8 |
| 7,468,032 B2* | 12/2008 | Stahmann et al. | 600/301 |
| 7,774,052 B2* | 8/2010 | Burton et al. | 600/544 |
| 8,639,520 B2* | 1/2014 | Finn et al. | 705/2 |
| 2003/0055679 A1* | 3/2003 | Soll et al. | 705/2 |
| 2003/0092975 A1* | 5/2003 | Casscells et al. | 600/300 |
| 2003/0225315 A1* | 12/2003 | Merrett et al. | 600/300 |
| 2003/0233250 A1* | 12/2003 | Joffe et al. | 705/2 |
| 2004/0039262 A1 | 2/2004 | Bardy | |
| 2004/0054261 A1 | 3/2004 | Kamataki et al. | |
| 2004/0111296 A1 | 6/2004 | Rosenfeld et al. | |
| 2004/0148140 A1 | 7/2004 | Tarassenko et al. | |
| 2004/0237202 A1 | 12/2004 | Gallant et al. | |
| 2004/0249299 A1* | 12/2004 | Cobb | 600/529 |
| 2004/0249676 A1* | 12/2004 | Marshall et al. | 705/2 |
| 2005/0004485 A1* | 1/2005 | Crosby et al. | 600/513 |
| 2005/0240438 A1* | 10/2005 | Day | 705/2 |
| 2005/0256415 A1* | 11/2005 | Tan et al. | 600/509 |
| 2006/0025824 A1* | 2/2006 | Freeman et al. | 607/5 |
| 2006/0200009 A1* | 9/2006 | Wekell et al. | 600/300 |
| 2007/0172907 A1* | 7/2007 | Volker et al. | 435/15 |

OTHER PUBLICATIONS

Knaus, W. A., et al.; Clinical Investigations in Critical Care; The Apache III Prognostic System; Risk Prediction of Hospital Mortality for Critically Ill Hospitalized Adults; 1991; Chest; 100(6)1619-1636.

* cited by examiner

APPARATUS TO MEASURE THE INSTANTANEOUS PATIENTS' ACUITY VALUE

CROSS REFERENCE TO RELATED APPLICATIONS

This application claims the benefit of U.S. provisional application Ser. No. 60/692,754 filed Jun. 22, 2005, which is incorporated herein by reference.

The following relates to medical arts. It finds particular application in conjunction with the collection, analysis and display of the patient information at the hospitals and will be described with particular reference thereto. However, it is to be appreciated that the present invention is applicable to patient monitoring, diagnosing, and the like at the health care facilities such as home care facilities, nursing homes and the like for a variety of health care applications.

Typically, patients in intensive/coronary care units (ICU/CCU) are connected to a plurality of technologically sophisticated instrumentation that provides detailed measurements of the pathophysiological state of each patient. There is a growing volume of relevant data from clinical observations, bedside monitors, mechanical ventilators and a wide variety of laboratory tests and imaging studies. The abundance of data and its poor organization makes its integration and interpretation time-consuming, inefficient, and increasingly complex. Such "information overload" may actually hinder the diagnostic process, and may even lead to neglect of relevant data, resulting in errors and complications in ICU care.

In an effort to help ensure adequate clinical coverage, current approaches predict the index of mortality of the patient at the time the patient is admitted to the intensive care unit or the like. For example, when the patient is admitted to the health care facility, patient information is collected and tests and measurements are performed to estimate the risk of mortality. There are few methods to calculate a mortality index, one of which is to calculate a Simplified Acuity Physiology Score (SAPS) that is a snapshot of the patient's physiological condition at the time of admission. SAPS is calculated by assigning a predetermined number of points to certain medical conditions, measurements, medical data, and the like. However, the acuity scores provided by the current methodologies are not adequate predictors of the patient deterioration.

Some of the common pathways for deterioration of a patient's condition in the intensive care unit is single-organ system failure (SOSF) and multi-organ system failure (MOSF). Although SOSF and MOSF have multiple causes, the deterioration in the function of a single or multiple organ systems frequently indicates that the patient's condition is worsening which, more likely than not, would result in a poor outcome for the patient. Identifying the development of SOSF or MOSF in the early stages by identifying the initial signs of the patient deterioration would help with earlier treatment for the patients who experience the deterioration in the function of single or multiple systems and typically improve the outcome of the treatment.

There is a need to utilize incoming clinical data as it becomes available to detect and display clinically significant information and produce alarms to warn the clinical staff about the clinically significant events. The present application contemplates a new and improved method and apparatus that overcomes the above-referenced problems and others.

SUMMARY OF THE INVENTION

In accordance with one aspect of the present application, a patient monitoring system is disclosed. At least one sensor senses shorter interval physiological parameters of a monitored patient. Longer interval data of the monitored patient are collected in at least one database. A composite acuity score generator generates or updates a composite acuity score indicative of wellbeing of the patient based at least on the sensed physiological parameters and the longer interval data. A monitor automatically displays at least current values of at least one of selected sensed physiological parameters, longer interval data, and the composite acuity score.

In accordance with another aspect, a monitoring method is disclosed. Shorter interval physiological parameters of a patient are sensed. Longer interval data of the patient are collected. One or more composite acuity scores indicative of wellbeing of the patient are generated based at least on one of the sensed physiological parameters and the longer interval data. At least current values of at least one of selected sensed physiological parameters, longer interval data, and the composite acuity score are displayed.

One advantage of the present invention resides in faster presenting of critical patient acuity information to the health care professionals.

Another advantage resides in predicting patient instability before the patient actually becomes unstable.

Another advantage resides in presenting an alarm or alert that calls attention to health care professionals that critical patient acuity information is available.

Another advantage resides in generating a dynamically updated acuity score of the patient.

Another advantage resides in being able to view all current key information that is triggering the current critical condition.

Another advantage resides in being able to view the changes that have occurred to key information that is triggering the current critical condition so that corrective action can be initiated.

Another advantage resides in being able to generate a permanent record of events triggering the current critical condition and the effects of action that was taken.

Another advantage resides in maintaining a quality patient care.

Another advantage resides in generating correlated patient acuity and medical care path reports.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1:
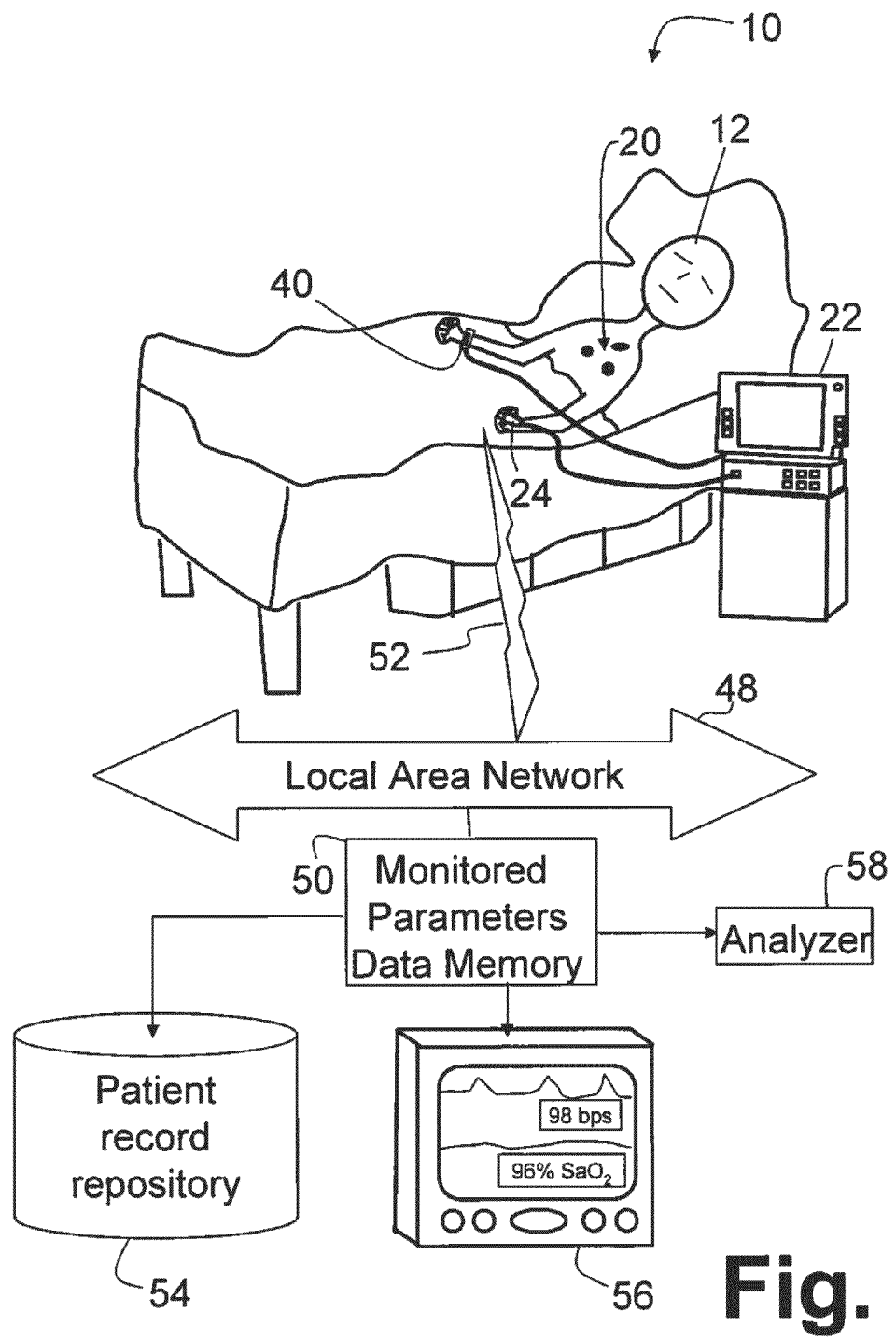
FIG. 1 is a diagrammatic illustration of a patient monitoring system.

With reference to FIG. 1, a patient monitoring system 10 analyzes physiological information over a period of time to determine the wellbeing of a patient 12, e.g. whether the patient's condition is improving, stabilizing, or deteriorating. The patient monitoring system 10 monitors wellbeing of the patients with various conditions such as postoperative recovery patient, emergency care unit patients, infants susceptible to sudden infant death syndrome, and others. The bedside monitor 22 measurements are collected in very short intervals as some medical conditions require urgent intervention. Other data (clinical observations, lab tests, medication administration, imaging studies, etc) are collected in longer time intervals.

In the illustrated example, the patient monitoring system 10 includes a wireless or wired patient point-of-care network which includes: (i) sensor nodes 20 disposed on the patient 12 to monitor vital signs such as electrocardiographic (ECG) data, heart rate, respiratory rate, respiratory cycle, blood pressure, or so forth; and (ii) a bedside blood oxygen saturation ($SpO_2$) monitor 22 connected with an $SpO_2$ fingertip probe 24. The wireless or wired point-of-care network is an example, and those skilled in the art can readily include additional or other medical devices such as high resolution sensors and bedside monitors and ventilators in the network. Moreover, the wireless point-of-care network can be changed on an ad hoc basis by adding or removing medical devices.

It will be appreciated that wires or cabling are not necessarily completely omitted from the wireless patient point-of-care network—for example, the $SpO_2$ fingertip probe 24 may be connected with the $SpO_2$ monitor 22 by a cable. Similarly, although not illustrated, it is contemplated that some of the devices of the patient point-of-care network may include power cords connected to house electricity. For example, although the illustrated, the $SpO_2$ monitor 22 is battery-powered, it could instead or additionally include a power cord plugged into a conventional electrical power outlet.

The patient point-of-care network further includes a patient identification device 40. In the illustrated embodiment, the patient identification device 40 is disposed on a wristband worn by the medical patient 12; however, more generally the patient identification device 40 can be worn or attached to the patient 12 substantially anywhere. The medical devices 22, 24 optionally also wirelessly communicate with each other. The patient identification device 40 optionally also includes patient monitoring or therapy functionality, such as an ECG, $SpO_2$, or other sensor.

The wireless data communication with a local area network 48 of the hospital or other medical facility is diagrammatically indicated in FIG. 1 by a jagged connector 52. The collected data is stored at a monitored parameters data memory 50 and can be transferred to a patient record repository 54, displayed on a vital signs monitoring station or surveillance center or display 56, compared with previous sensor readings, or otherwise utilized for patient monitoring and treatment evaluation. Indeed, once the collected data is sent to and stored in the patient record repository 54, it can be used by any device on the network 48 which has the proper authorization to access it. For example, the collected data can be sent back to the bedside monitor 22 or vital signs monitoring station or surveillance center or display 56 via the local area network 48.

A physiological information analyzer 58 receives physiological information from one or more sensors, bedside patient monitors, and ventilators for short interval data, as well as longer interval relevant data from clinical observations, laboratory tests, medication administration records, and imaging studies, all of which are linked to the patient 12 to obtain and monitor physiological information. The analyzer 58 collects and processes the fused data to generate a visual representation such as a graph or a numerical value and/or an audio signal such as, for example, an alert or an alarm that a Patient Index has exceeded a critical limit. The medical professional takes notice of the alert or alarm and displayed clinical information and makes the decisions whether the intervention necessary, at what time, and to what extent.

Figure 2:
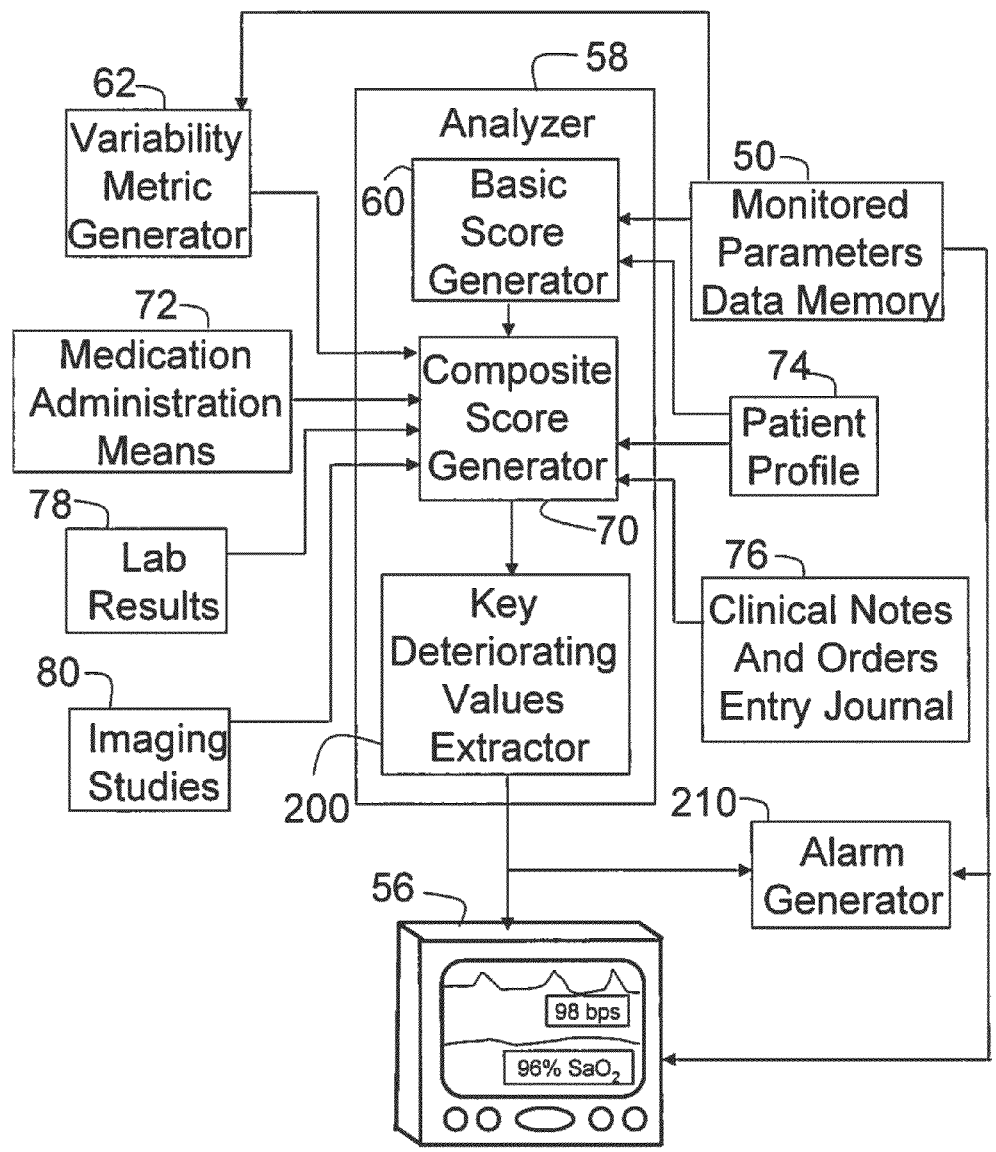
FIG. 2 is a diagrammatic illustration of a portion of the patient monitoring system.

With continuing reference to FIG. 1 and further reference to FIG. 2, the physiological information analyzer 58 continually calculates a severity of an illness of the patient 12 for one or more Patient Indices (PI) that is expressed as composite acuity score(s). More specifically, a basic score generator 60 maps the detected measurement results along with the other information to a scoring system. E.g., a number of points is given to measurement values, clinical observations, patient condition, etc. The number of points, which is given to a particular measurement value and other categories, is predetermined in advance. Initially, the basic score is determined for the newly admitted patient. For example, a first value of each variable measured within an initial time period, such as a time from an initial contact with the patient at the intensive care unit to one hour after the patient arrival to the intensive care unit, is taken. Of course, the initial contact may happen in an emergency room, at home, at the ambulance, and the like. For example, Systolic Blood Pressure, which is measured greater than or equal to 200 mm Hg, is given a score of 2. If Systolic Blood Pressure is measured between 70 and 99 mm Hg, it is given a score of 5; if less than 70 mm Hg, it is given a score of 13, else, if between 100 and 199 mm Hg, the score is 0. In this manner, the certain measurement values and medical conditions of predefined categories are given a certain score, as, for example, outlined in the Table 1 below.

TABLE 1

| | Record the number in square brackets if the condition is present: |
|---|---|
| (1) | Age in years:<br>[0] <40<br>[7] 40-59<br>[12] 60-69<br>[15] 70-74<br>[16] 75-79<br>[18] >=80 |
| (2) | Heart Rate in beats per minute:<br>[11] <40<br>[2] 40-69<br>[0] 70-119<br>[4] 120-159<br>[7] >=160 |
| (3) | Systolic blood pressure, mm Hg:<br>[13] <70<br>[5] 70-99<br>[0] 100-199<br>[2] >=200 |
| (4) | Body Temperature in ° C.:<br>[0] <39<br>[3] >=39 |
| (5) | If on ventilation or CPAP PaO2/FIO2:<br>[11] <100<br>[9] 100-199<br>[7] >=200 |
| (6) | Urinary Output in L per 24 hours:<br>[11] <0.500<br>[4] 0.500-0.999<br>[0] >=1.000 |
| (7) | Serum Urea Nitrogen in mg/dL:<br>[0] <28<br>[6] 28-83<br>[10] >=84 |
| (8) | WBC count in 1000 per μL:<br>[12] <1.0<br>[0] 1.0-19.9<br>[3] >=20 |

TABLE 1-continued

Record the number in square brackets if the condition is present:

| | | |
|---|---|---|
| (9) | Serum Potassium in mEq/L: | |
| | [3] <3.0 | |
| | [0] 3.0-4.9 | |
| | [3] >=5.0 | |
| (10) | Serum Sodium in mEq/L: | |
| | [5] <125 | |
| | [0] 125-144 | |
| | [1] >=145 | |
| (11) | Serum Bicarbonate in mEq/L: | |
| | [6] <15 | |
| | [3] 15-19 | |
| | [0] >=20 | |
| (12) | Bilirubin Level in mg/dL: | |
| | [0] <4.0 | |
| | [4] 4.0-5.9 | |
| | [9] >=6.0 | |
| (13) | Glasgow Coma Score: | |
| | [26] <6 | |
| | [13] 6-8 | |
| | [7] 9-10 | |
| | [5] 11-13 | |
| | [0] 14-15 | |
| (14) | Chronic Diseases: | |
| | [9] Metastatic Carcinoma | |
| | [10] Hematologic Malignancy | |
| | [17] AIDS | |
| (15) | Type of Admission: | |
| | [0] Scheduled Surgery | |
| | [6] Medical | |
| | [8] Unscheduled Surgery | |

The basic score generator 60 updates the basic score of each defined category in a nearly real-time. A variability metric generator or means 62 determines a variability metric of one or more measurement values such as a heart rate variability metric. A rapid change in the heart rate, blood, pressure, and other measurement values of the patient 12 during a prespecified time period might point to a worsening condition of the patient 12.

A composite acuity score generator or processor or means 70 automatically determines one or more real time composite acuity score(s) by receiving at least the updated basic acuity score(s) from the basic score generator 60, an updated variability metric from the variability metric generator 62, medication information from a medication administration processor or means 72, patient data from a patient profile 74, physician's notes and nurse's notes from a clinical notes and orders entry journal 76, laboratory test results from lab results 78, imaging results from imaging studies 80, and other like data.

As described above, the physiological information analyzer 58 continually calculates a severity of an illness of the patient 12 for one or more Patient Indices (PI) that is expressed as composite acuity score(s).

Figure 3:
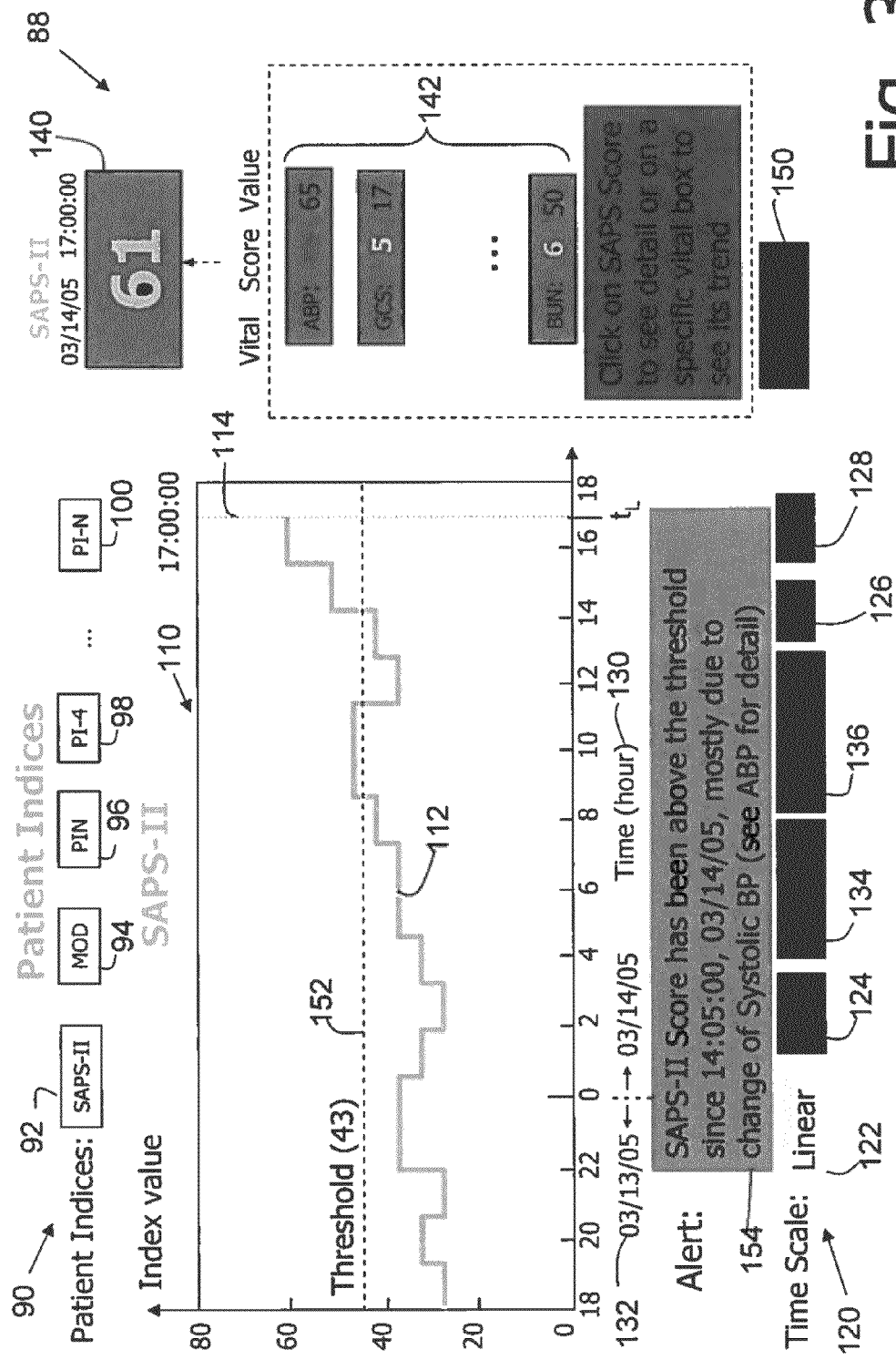
FIGS. 3-7 show Patient Indices displays.
Figure 4:
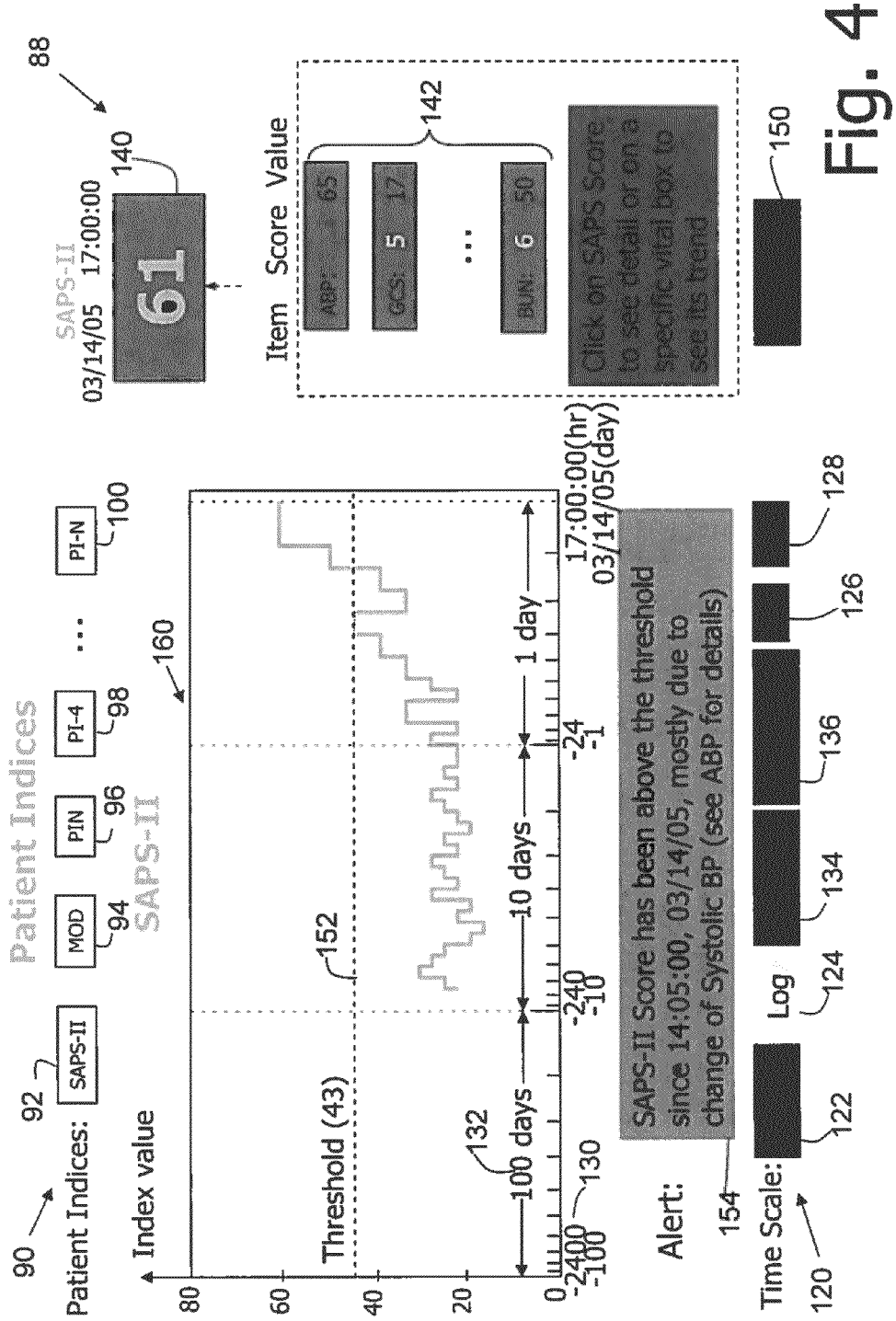

With reference to FIGS. 3 and 4, a home screen 88 of the patient display is shown. A patient indices selection row or boxes 90 includes an exemplary list of the patient acuity indices (PI). Example of one such PI is a real-time extension to the clinically accepted SAPS-II (Simplified Acute Physiology Score) 92, a score which correlates with a patient's mortality rate in the ICU. The real-time extension of SAPS-II conveniently provides for the initial calculation of the SAPS-II score as well as a continuously updated SAPS-II score that is capable of detecting and showing patient deterioration. Another example of PI is MOD (Multi-Organ Dysfunction Score) 94, a score which correlates with the likelihood of multi-organ failure in the ICU. Another example is PIN (Physiological Instability Numeric) 96, a uniquely defined feature vector score that correlates with the current physiological instability of the patient in the ICU. Icons 98, . . . , 100 labeled "PI-4", through "PI-N" may be any currently accepted or future Patient Indices.

By clicking on any of the icons in the patient indices row 90, the corresponding patient index information is displayed. In FIG. 3, the real time SAPS-II index is currently selected, as the icon "SAPS-II" is highlighted.

With continuing reference to FIG. 3, the home screen 88 includes a linear scaled graphic window 110 showing a patient index trend or SAPS-II score curve 112 over time. The latest (or current) time $t_L$ for the patient index curve 112 is placed at a point close to the right end of the window 110 and marked with a vertical cursor or mechanism 114. The time scale can be controlled through "Time Scale" control icons 120 at the bottom row. The time scale controls include: Linear scale 122, Log scale 124, Left (<-) and Right (->) cursor controls 126, 128, which allow the user to transverse or move through the trend data to see how the Vitals and PI Scores have changed over time. Likewise, the user may jump to a specific time in the trend by placing the cursor over that area and left-clicking the mouse. The standard or default window is a 24-hour window in the Linear scale with current time at the right. A time label 130 is marked backward from the current time to allow the window 110 to cover 24-hour data prior to the current time. A date label 132, shown beneath the time label, indicates which portion of the window 110 belongs to which date. By clicking on "Zoom In", "Zoom Out" icons 134, 136 the user can enlarge or reduce a portion of the window 110.

The composite acuity score or patient index or overall SAPS-II score value at the current time $t_L$ is displayed in a SAPS-II score window 140 at the right side of the screen 88. Individual parameters' scores and vital values contributing to the overall SAPS-II score are displayed in vital item boxes 142. For example, the parameters include arterial blood pressure (ABP), Glasgow coma score (GCS), and blood urea nitrogen (BUN), and others for calculation of the SAPS-II score value. The default position of the vertical cursor 114 is at the current time $t_L$, thus the current SAPS-II score and its details are shown in the real-time manner. The cursor 114 can be moved to any position of the window 110 and the SAPS-II score and its details at that time point are correspondingly displayed along with the date and time.

By clicking the "Table List" button 150 at the right bottom corner of the screen 88, all SAPS-II scores and individual variable values and scores can be displayed in a table with time and date.

An adjustable threshold level 152 in the graphic window 110 within the SAPS-II score curve 112 sets an allowable value for the SAPS II score. When the SAPS-II score exceeds the threshold, an alerting message can be issued on the screen 88, as seen in a "Alert" message box 154.

With reference again to FIG. 4, clicking the "Log" icon 124 in the "Time Scale" control row 120, a SAPS-II log scaled graphic window 160 using a log scale with 10 as the base is displayed. The log graphic window 160 is functionally similar to the linear graphic window 110, except that the time scale in the log graphic window 160 is in a logarithmic scale. For the time label 130, the starting time is the current time, e.g. 17:00:00, at the right end of the log window 160. The time is backward labeled in hours in the log scale. The numbers that show time are negative as referring to the past time. In the date label 132, the starting date is the current day, e.g. Mar. 14, 2005, as shown in the right end of the window. The date is backward labeled in days in the log scale. The numbers that show date are negative as referring to the past date. In the log time scale, the data can be viewed in a very large time scope, with emphasis and more detail in recent data and less detail in long-before data. The SAPS-II score value and its contributing individual variables' scores and values at the position of the vertical cursor 114 are displayed in the right part of the screen 88. The cursor 114 can be moved to any place in the window 160 where the data are available and the corresponding SAPS-II score and its detailed contributions are shown accordingly.

Figure 5:
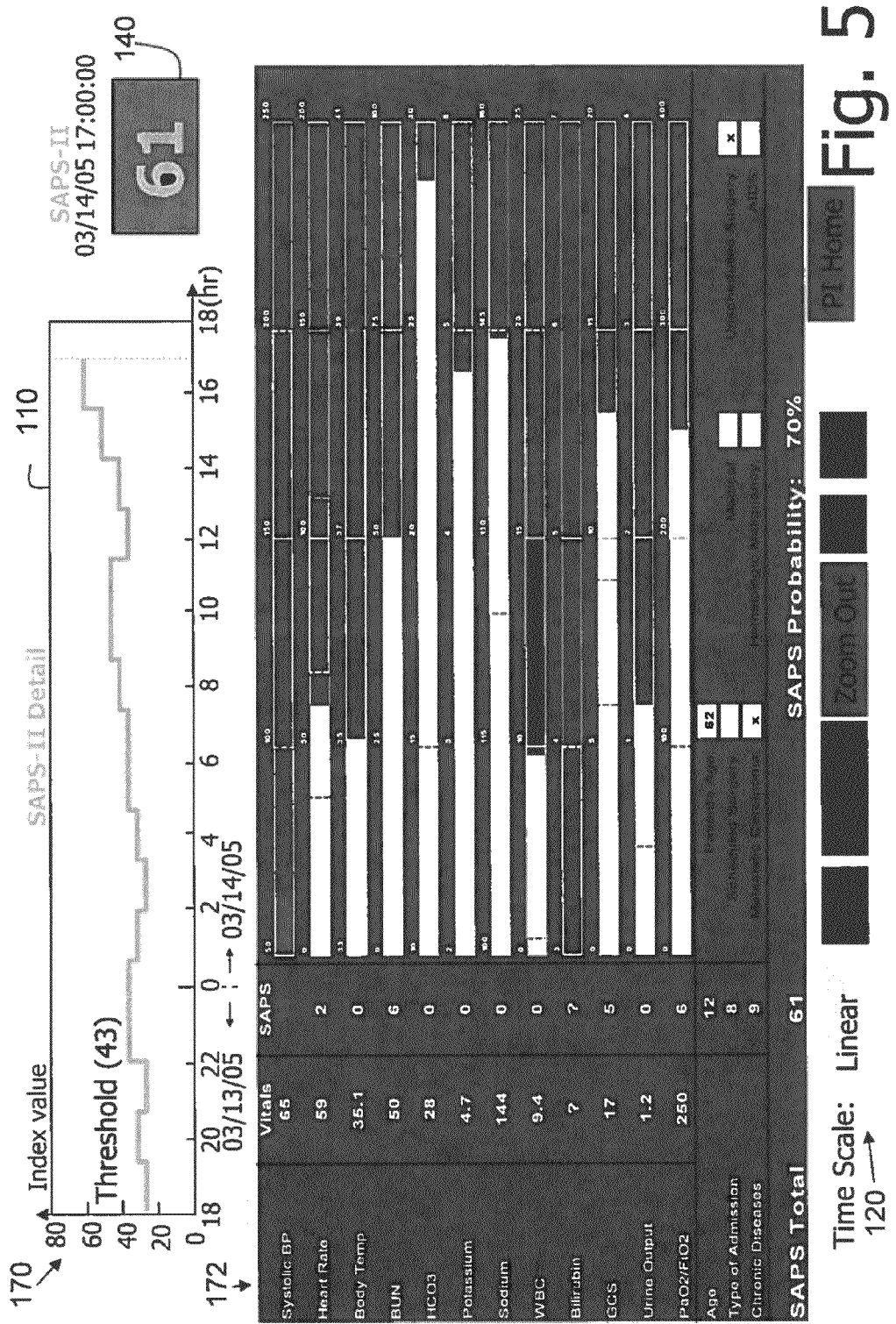

With reference to FIG. 5, by clicking within the overall SAPS-II score window 140, the detailed individual components of the SAPS-II patient index are displayed along with the overall SAPS Score and SAPS Probability of Mortality. A reduced SAPS-II Score graphic window 110 is shown in a top panel 170 of the screen. As discussed above, the graphic window includes Time Scale control icons 120 and the position of the vertical cursor 114 as previously chosen. All SAPS-II individual components are displayed for the time indicated by the cursor position in a lower panel or detailed component display 172 of the screen 88. All pre-established and set SAPS-II thresholds as well as the individual component "Vitals" and "SAPS" scores and graphical indicators are shown for each component. Other non-varying components such as Age, Type of Admission and Chronic Diseases are shown for entry and display purposes. The individual component SAPS scores as well as the Overall SAPS Score and SAPS Probability are all automatically calculated and displayed for the selected position of the vertical cursor 114. The vertical cursor 114 can be moved in each window as previously described.

The "Table List" control icon is replaced with a "PI Home" control icon, which returns the user to the "Patient Indices Home" display.

Figure 6:
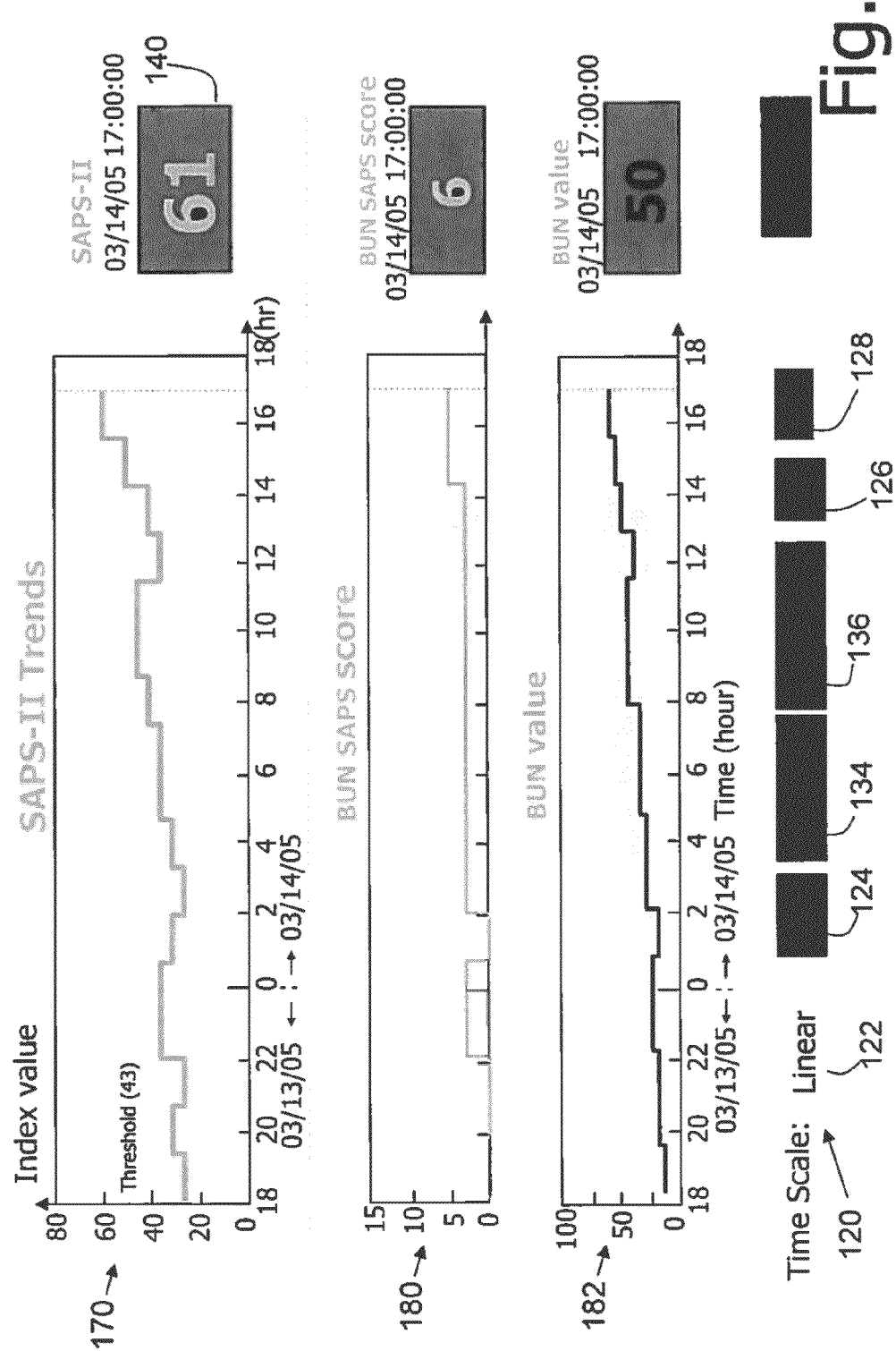
Figure 7:
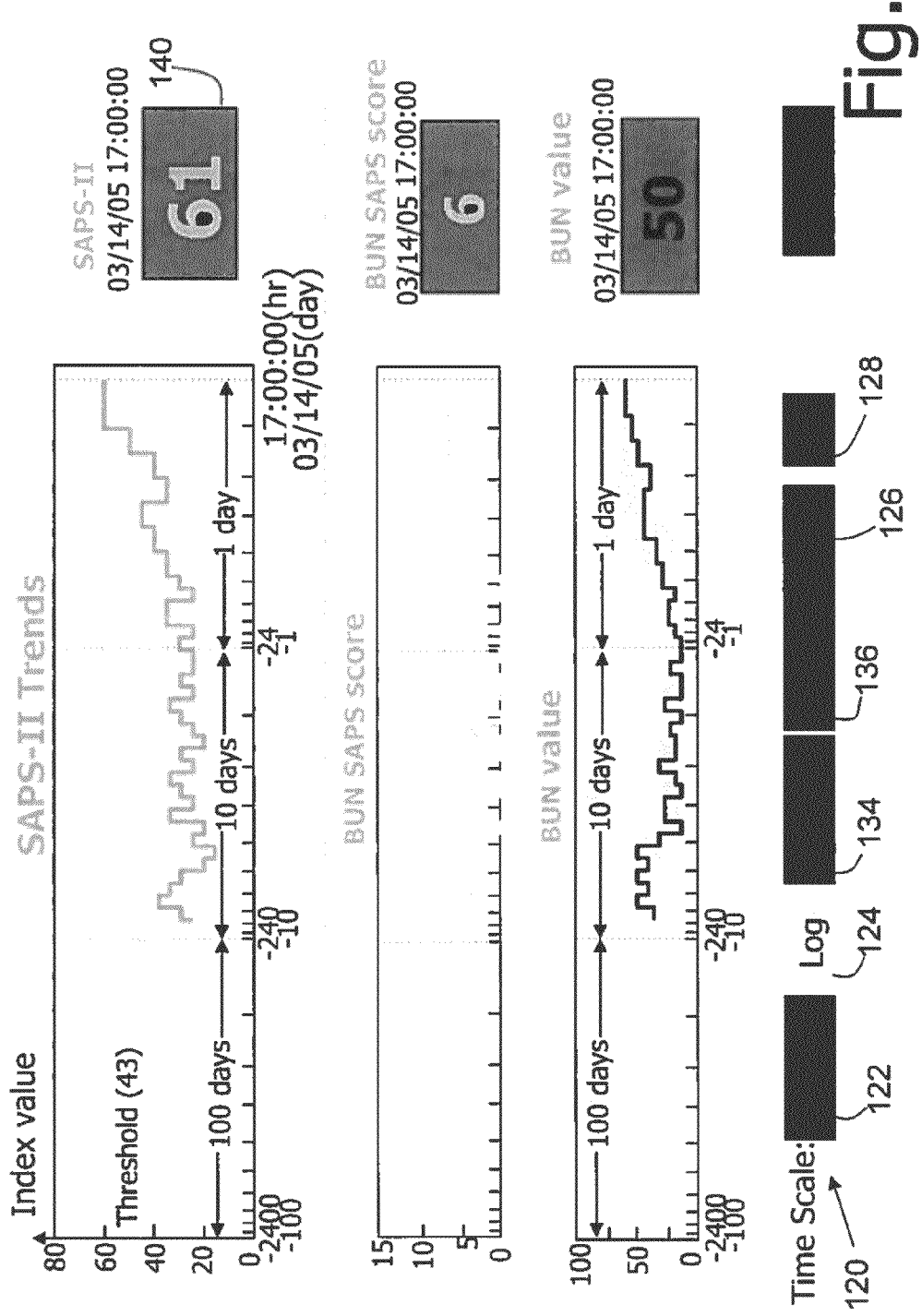

With reference to FIGS. 6 and 7, by clicking any of the vital item boxes 142 on the screen 88, e.g. such as BUN-box, detailed trends information about the particular variable can be displayed along with the overall SAPS-II trend and score. FIG. 6 shows a linear scale, while FIG. 7 shows a log scale. The top panel 170 is the overall SAPS-II trend window and a SAPS-II score value at the cursor point. Middle and lower panels or trend displays 180, 182 show the BUN's individual SAPS score and BUN value in the time window corresponding to the overall SAPS-II score window. The BUN SAPS score and BUN value at the cursor time point are shown in the right side of the screen.

The "Time Scale" control icons 120 are available. The "Table List" control icon is replaced with a "PI Home" control icon, which returns the user to the "Patient Indices Home" display.

The vertical cursors can be moved in each window as previously described. The Vital values and SAPS score at the cursors' positions are accordingly displayed.

Figure 8:
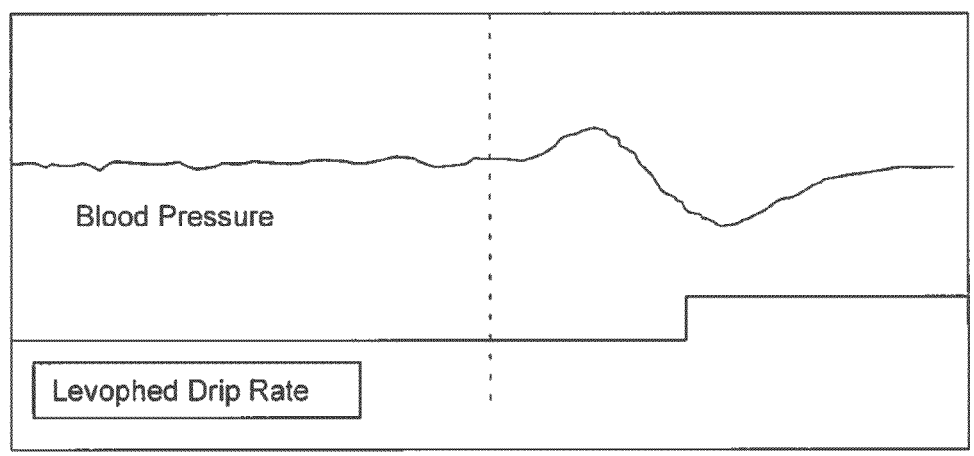
FIG. 8 is a graphical representation of a blood pressure measurement and a medication drip rate.

With reference to FIG. 8, the patient's condition is stable for a period of time until there is an increase in blood pressure for a short period of time. Increase in the blood pressure is followed by a precipitous drop in blood pressure. Such drop in the patient's blood pressure might be indicative of the beginning of the hemodynamic instability of the patient 12. This point in time can serve as a fiducial point at which the condition of the patient 12 starts worsening. After clinical observation, the drip rate of the medication is increased which is calculated to correct the patient's deterioration. This condition and others would automatically alert medical professionals to take notice of the displayed information of this clinically significant change, and make decisions whether the intervention is necessary, at what time, and to what extent.

The continually updated composite score(s) indicate the wellbeing of the patient 12 and predicts when the worsening physiological trend would reach the point indicating that intervention is necessary to alter the patient outcome in a positive way.

Figure 9:
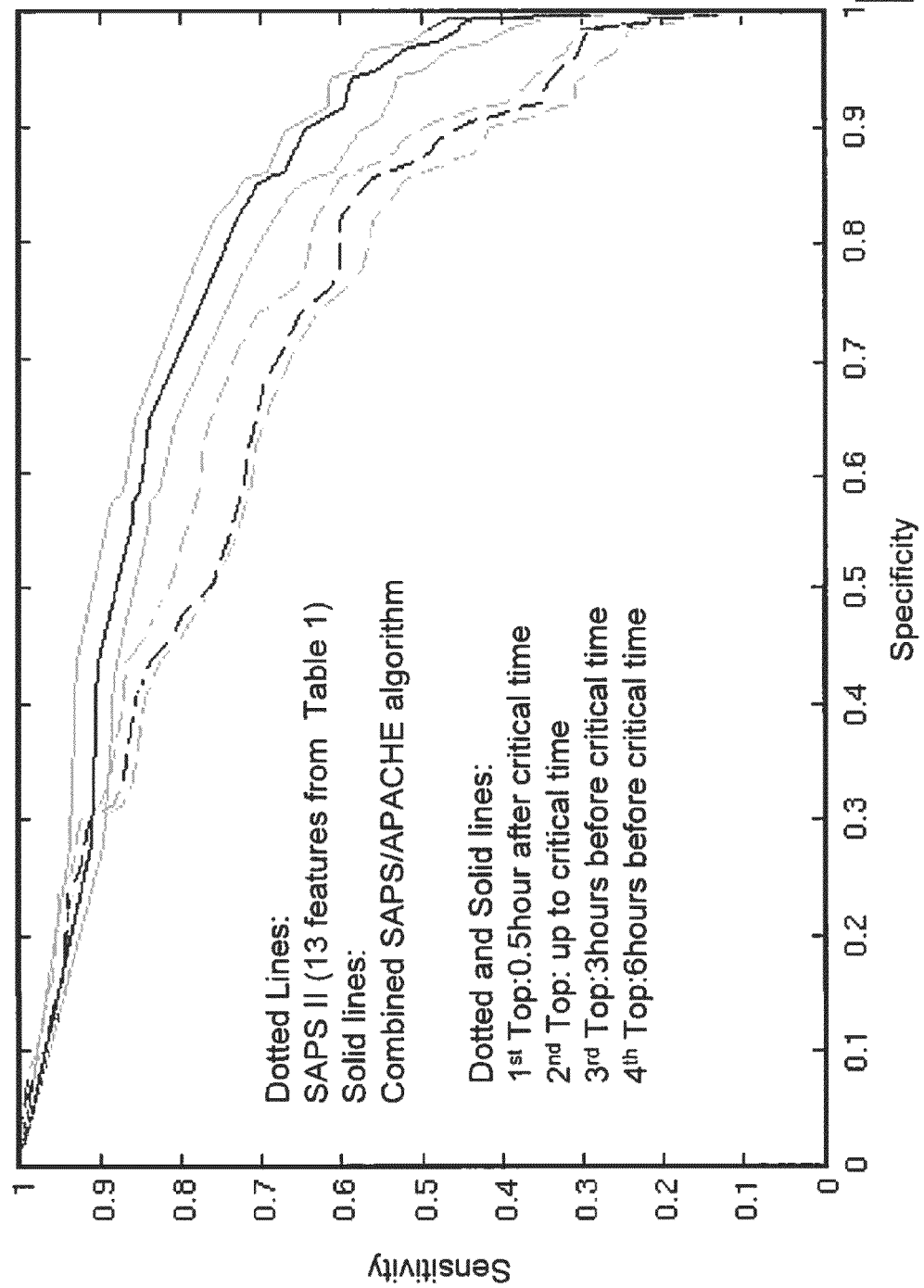
FIG. 9 is a set of ROC curves.

With reference to FIG. 9, the ROC curves are shown. As known in the art, the ROC curves represent a tradeoff between the sensitivity and specificity. The dotted curves use the first thirteen SAPS II features of the Table 1 and show that sensitivity and specificity, of need for intervention, improve as time moves closer to actual intervention. This shows that there is value in continuously updating the SAPS II score.

The solid curves use the same thirteen SAPS II features, as used in the dotted curves and, in addition, Hematocrit, which is one of the features of the APACHE algorithm. As shown, by adding one additional feature, a considerable improvement is made toward being able to show the need for intervention. By supplementing the continually updated basic acuity scores with additional measurements and parameters such as heart rate variability (HRV), anion gap, estimated cardiac output, blood lactic acid, A-a gradient, and other readily available clinical and physiological measurement values, single-organ system failure, multi-organ system failure, physiological instability as well as other serious conditions of the patient 12 are detected in earlier stages. Each of the above listed early warning signals individually is not typically a reliable predictor of the patient deterioration, but when taken collectively as a 'feature vector'; the early warning signals they can become an extremely reliable predictor. The improved sensitivity and specificity of shown ROC curves over the SAPS-II individual performance shows this reliability.

With reference again to FIG. 2, in one embodiment, a key deteriorating values extractor 200 extracts key deteriorating values. Information pertinent to the key parameters that cause deterioration is displayed on the display 56. For example, pulse irregularities can cause an ECG signal to be displayed. The key deteriorating values extractor 200 additionally performs continuous analysis of the trend data searching for unexpected clinically significant changes. Clinically unexpected significant changes as well as the lack of expected physiological change to drugs are examples of the key extracted features. Such analysis and display of the information provides a strategic decision support. The medical personnel can make enhanced strategic plans for the wellbeing of the patient 12 with anticipation to positively alter patient's outcome which, for example, includes death, discharge to home, and discharge to other care units/settings.

An alarm generator 210 generates an alarm or alert. For example, if one of the monitored individual parameter values exceeds a corresponding threshold value an alert might be issued. As another example, if the composite acuity score exceeds a corresponding threshold value, the alarm generator generates the alarm which is provided to the medical personnel. The alarm might be set as a tone, a voice signal, or a display of a textual message on the display 56. If the alarm caused by an individual parameter value, the medical personnel can address the respective physiological function that caused the alarm. For example, if the heart rate is too low or if blood pressure is too low and dropping, the medical personnel takes the appropriate steps which typically lead to increasing the heart rate and/or blood pressure. Alarms of different levels, such as a caution or watch level, a critical level, an immediate intervention level, and the like can be generated as different thresholds or combinations of thresholds, or composite thresholds are reached or exceeded.

If the alarm is caused by the composite acuity score, such alarm indicates to the medical personnel that the patient is deteriorating in some way. The medical personnel determines the necessity, time and nature of therapeutic intervention.

Examples of major therapeutic interventions are the use of intra-aortic balloon pumps, vaso-active medications, large fluid boluses, and significant blood transfusions.

In one embodiment, the data provided by the monitoring system 10 is analyzed to retrospectively determine how the medical personnel reacted to certain acuity scores and how the interventions affected the patient outcome. The administrator can evaluate how well the medical personnel managed hemodynamic instability of the patient, transient instability of the patient, and so forth. By looking at the change in the acuity scores, the administrator can modify the unit performance and interventional procedures to enhance the wellbeing of the patient.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A patient monitoring system comprising:
   at least one sensor which senses physiological parameters of a monitored patient in real time;
   at least one database which stores interval data of the monitored patient collected at temporally spaced intervals;
   a processor programmed to:
      continually receive the currently sensed physiological parameters of monitored patient from the at least one sensor,
      retrieve the stored interval data from the database,
      continually calculate a real time acuity score in real time indicative of at least one of current wellbeing, a current risk of mortality, a current likelihood of single or multi-organ failure, and a current physical instability of the patient based at least on a composite of the sensed physiological parameters and the interval data such that the current acuity score changes as the sensed physiological parameters change;
      compare the real time acuity score with a threshold; and
      determine at least one of (1) the sensed current physiological parameters primarily responsible for the acuity score reaching the threshold and (2) the sensed current physiological parameters that are significant to medical personnel deciding a course of action for altering and enhancing the patient's current physiological condition; and
   a monitor which concurrently displays in real time the current values of (1) at least a selected one of the physiological parameters values sensed in real time, and (2) at least a selected one of the interval data, and (3) the calculated real time acuity score, and (4) the determined significant sensed current physiological parameters.

2. The system as set forth in claim 1, wherein the processor is further programmed to:
   map values of at least the sensed physiological parameters to points of a scoring system which preassigns points to sensed physiological parameter values; and
   generate a basic acuity score of the patient from the points.

3. The patient monitoring system as set forth in claim 1, wherein the monitor is a bedside monitor.

4. The patient monitoring system as set forth in claim 1, wherein the calculated real time acuity score includes a Simplified Acuity Physiology Score (SAPS).

5. The patient monitoring system as set forth in claim 1, wherein calculating the real time acuity score includes:
   generating basic acuity score values including:
      preassigning points to at least each sensed physiological parameter, and
      mapping values of the sensed physiological parameter to the preassigned points;
   continually updating the basic acuity score in real time based at least on the sensed physiological parameters; and
   updating the real time acuity score based on the updated basic acuity score in real time.

6. The system as set forth in claim 1, wherein the interval data includes at least one of:
   medication administration record;
   patient's profile data;
   clinician notes and orders from physician's and nurse's entry journal;
   laboratory data;
   imaging data; and
   physiological parameter variability metric indicative of a trend in the patient wellbeing change.

7. The patient monitoring system as set forth in claim 1, wherein the processor is further programmed to:
   calculate a trend depicting changes in the real time acuity score versus time; and
   provide the calculated trend to the monitor to be displayed.

8. The patient monitoring system as set forth in claim 1, wherein the processor is further programmed to:
   determine which of the sensed physiological parameters are significant to medical personnel deciding a course of action for altering and enhancing the patient's current physiological condition; and
   provide the determined current physiological parameters to the monitor to be displayed.

9. A patient monitoring system comprising:
   at least one sensor which continually senses current physiological parameters of a monitored patient in real time;
   at least one database which stores interval data of the monitored patient generated at intervals;
   a processor programmed to:
      continually receive the currently sensed physiological parameters of monitored patient from the at least one sensor,
      retrieve the stored interval data from the database,
      map values of at least the sensed physiological parameters to a scoring system which assigns points based on the sensed physiological parameters,
      generate a current basic acuity score in real time based on the scoring system points assigned based on a composite of the sensed physiological parameters,
      continually automatically update the current basic acuity score in real time as the currently sensed physiological parameters change, and
      generate a current composite acuity score in real time indicative of wellbeing of the patient based on the current basic acuity score and the interval data;
      compare the composite acuity score with a threshold; and
      determine at least one of (1) the sensed current physiological parameters primarily responsible for the acuity score reaching the threshold and (2) the sensed current physiological parameters that are significant to medical personnel deciding a course of action for altering and enhancing the patient's current physiological condition; and a monitor which displays in real time at least current values of the current composite acuity score and at least one of the currently sensed physiological parameters values and the determined significant sensed current physiological parameters.

10. The system as set forth in claim 9, wherein the interval data includes at least one of:
medication administration record;
patient's profile data;
clinician notes and orders from physician's and nurse's entry journal;
laboratory data;
imaging data; and
physiological parameter variability metric indicative of a trend in the patient wellbeing change.

11. The system as set forth in claim 9, further including:
an alarm generator which generates an alarm in response to the current composite acuity score reaching the threshold.

12. The system as set forth in claim 9, further including:
an alarm generator for generating one of a video and audio alarm for medical personnel, which generated alarm includes at least one of text, graphics, sound, vibration, color accents at least in response to one of the current physiological parameter value exceeding a first predetermined threshold and the current composite acuity score exceeding a second predetermined threshold.

13. The system as set forth in claim 9, wherein the sensed physiological parameters include a plurality of an Electrocardiogram (ECG), an Electroencephalogram (EEG), an Electromyogram (EMG), an invasive blood pressure (BP), a non-invasive blood pressure (NiBP), pulse, cardiac output, respirations, blood oxygen ($SpO_2$), and core body temperature.

14. The patient monitoring system as set forth in claim 9, wherein the monitor is a bedside monitor.

15. The patient monitoring system as set forth in claim 9, wherein the processor is further programmed to:
calculate a trend depicting changes in the current composite acuity score versus time; and
provide the calculated trend to the monitor to be displayed.

16. The patient monitoring system as set forth in claim 9, wherein the processor is further programmed to:
determine which of the current physiological parameters are significant to medical personnel deciding a course of action for altering and enhancing the patient's current physiological condition; and
provide the determined current physiological parameters to the monitor to be displayed in real time.

17. A patient monitoring system comprising:
at least one sensor which senses current physiological parameters of a monitored patient in real time;
at least one database which stores treatment and test data of the monitored patient;
a processor programmed to:
receive the sensed current physiological parameters form the at least one sensor,
retrieve the treatment and test data from the database,
generate and continuously update in real time a current composite acuity score indicative of wellbeing of the patient based at least on the sensed current physiological parameters and the treatment and test data, and
calculate a trend curve depicting a temporal evolution of the current composite acuity score; compare the composite acuity score with a threshold; and
automatically determine at least one of (1) the sensed current physiological parameters primarily responsible for the acuity score reaching the threshold and (2) the sensed current physiological parameters that are significant to medical personnel deciding a course of action for altering and enhancing the patient's current physiological condition; and
a monitor which displays a Patient Indices Interactive Display including:
a Patient Index Score Window which displays in real time the current composite acuity score of the patient, the displayed current composite acuity score being indicative of an overall current condition of the patient, and
a Patient Index Trend Curve which displays the trend curve in a graphic window.

18. The system as set forth in claim 17, wherein the trend curve is displayed in a logarithmic time scaled graphic window.

19. The system as set forth in claim 17, wherein the processor is further programmed to:
display a selected one or more of the sensed current physiological parameters and treatment and test data which contribute to the composite acuity score; and
control the display to display the selected current physiological parameters and the selected treatment and test data.

20. The system as set forth in claim 18, wherein the interval data includes at least one of:
medication administration record;
patient's profile data;
clinician notes and orders from physician's and nurse's entry journal;
laboratory data;
imaging data; and
physiological parameter variability metric indicative of a trend in the patient wellbeing change.

21. The system as set forth in claim 17, wherein the processor generates and updates a plurality of types of acuity scores and the monitor displays a plurality of acuity score boxes each of which displays one of the types of acuity score.

22. The system as set forth in claim 19, wherein the monitor further displays the trend curves for the selected physiological parameters and the selected treatment and test data which contribute to the displayed composite acuity score.

23. The system as set forth in claim 19, wherein the monitor further displays detailed values of the selected physiological parameters and the treatment and test data for the displayed composite acuity score for a selected time.

24. The system as set forth in claim 17, wherein generating the composite acuity score includes:
generating basic acuity score values including:
preassigning points to at least each sensed physiological parameter, and
mapping values of the sensed physiological parameter to the preassigned points;
continually updating the basic acuity score in real time based at least on the sensed current physiological parameters; and
updating the composite acuity score based on the updated basic acuity score.

25. The patient monitoring system as set forth in claim 17, wherein the processor is further programmed to:
determine which of the current physiological parameters are significant to medical personnel deciding a course of action for altering and enhancing the patient's current physiological condition; and provide the determined current physiological parameters to the monitor to be displayed.

26. A patient monitoring system comprising:
sensors which sense current physiological parameters of a monitored patient in real time;
at least one database which stores treatment and test data of the monitored patient;
a processor programmed to in real time:
generate and update an acuity score indicative of wellbeing of the patient based at least on the sensed current physiological parameters and the treatment and test data,
compare the acuity score with a threshold,
determine at least one of (1) the sensed current physiological parameters primarily responsible for the acuity score reaching the threshold and (2) the sensed current physiological parameters that are significant to medical personnel deciding a course of action for altering and enhancing the patient's current physiological condition;
a monitor which displays current values of the determined sensed current physiological parameters.

27. The system as set forth in claim 26, wherein the treatment and test data include at least one of:
medication administration record;
patient's profile data;
clinician notes and orders from physician's and nurse's entry journal;
laboratory data;
imaging data; and
physiological parameter variability metric indicative of a trend in the patient wellbeing change.

28. The patient monitoring system as set forth in claim 26, wherein the processor is further programmed to:
calculate a trend curve depicting changes in the acuity score versus time; and
display the calculated trend curve on the monitor with the acuity score.

29. The patient monitoring system as set forth in claim 28, wherein the processor is further programmed to:
continuously analyze the trend curve to find unexpected significant changes in the acuity score.

30. The patient monitoring system as set forth in claim 26, wherein the calculated real time acuity score includes a Simplified Acuity Physiology Score (SAPS).

31. The patient monitoring system as set forth in claim 26, wherein the processor is further programmed to:
calculate a ROC curve representing a tradeoff between sensitivity and specificity, wherein the ROC curve accounts for a plurality of early warning signals.

32. A patient monitoring system comprising:
at least one sensor which continuously senses current physiological parameters of a monitored patient;
at least one database which stores intermittently generated medical data of the monitored patient;
a means for generating and updating in real time one or more composite acuity scores indicative of wellbeing of the patient based at least on the sensed current physiological parameters received from the at least one sensor and the intermittently generated medical data received from the at least one database;
a means for comparing the composite acuity score with a threshold; and
a means for automatically determining at least one of (1) the sensed current physiological parameters primarily responsible for the acuity score reaching the threshold and (2) the sensed current physiological parameters that are significant to medical personnel deciding a course of action for altering and enhancing the patient's current physiological condition; and
a means for displaying current physiological parameter values and the generated and updated one or more composite acuity score in real time and the determined sensed physiological parameters.

* * * * *